United States Patent [19]

Palmer

[11] Patent Number: 4,501,698
[45] Date of Patent: Feb. 26, 1985

[54] PREPARING 1-(HYDROXYMETHYL)-TRIAZOLOBENZODIAZEPINES AND 1-(AMINOMETHYL)-TRIAZOLOBENZODIAZEPINES

[75] Inventor: John R. Palmer, Kalamazoo, Mich.

[73] Assignee: The Upjohn Company, Kalamazoo, Mich.

[21] Appl. No.: 480,978

[22] Filed: Mar. 31, 1983

[51] Int. Cl.$^3$ .......................................... C07D 487/04
[52] U.S. Cl. .............................. 260/245.5; 260/243.3; 260/244.4
[58] Field of Search ................ 260/244.4, 245.5, 243.3

[56] References Cited

U.S. PATENT DOCUMENTS

| | | | |
|---|---|---|---|
| 3,709,898 | 1/1973 | Hester, Jr. | 548/262 |
| 3,842,090 | 10/1974 | Gall et al. | 260/243.3 |
| 3,914,245 | 10/1975 | Gall | 548/262 |
| 3,947,466 | 3/1976 | Gall et al. | 548/269 |
| 3,992,393 | 11/1976 | Gall | 260/244.4 |
| 3,994,941 | 11/1976 | Hester | 260/245.5 |
| 3,995,043 | 11/1976 | Hester, Jr. | 424/263 |
| 4,001,262 | 1/1977 | Gall | 260/244.4 |
| 4,250,094 | 2/1981 | Hester, Jr. | 260/245.5 |

FOREIGN PATENT DOCUMENTS 2201210  8/1972  Fed. Rep. of Germany ... 260/245.5

OTHER PUBLICATIONS

Derwent Abstract 70853W/43 of CH 567-023 dated Sep. 30, 1975.
Derwent Abstract 70854W/43 of CH 567-024 dated Sep. 30, 1975.
Derwent Abstract 75881W/46 of CH 568-319 dated Oct. 31, 1975.
Derwent Abstract 35430T-B of Belgian 775558-Q dated May 19, 1972.
Derwent Abstract 48681A/27 of Japanese Patent Publ. No. J5 3059-696.
Derwent Abstract 52339T-B of W. German DT-22012-10-C.
Derwent Abstract 40575T-B of Belgian App. No. 776514-Q.

*Primary Examiner*—Alton D. Rollins
*Attorney, Agent, or Firm*—John T. Reynolds

[57] ABSTRACT

A process is provided for converting 1-hydrogen-triazolo[4,3-a]-[1,4]benzodiazepines, e.g., estazolam, to 1-(hydroxymethyl)-triazolo-[4,3-a][1,4]benzodiazepines, and, if desired, these 1-(hydroxymethyl)-compounds to 1-aminomethyl compounds, e.g., to adinazolam, without the need for column chromatography or sealed tube procedures, and while minimizing 1,4-bis-(hydroxymethyl)- group formation.

5 Claims, No Drawings

4,501,698

PREPARING 1-(HYDROXYMETHYL)-TRIAZOLOBENZODIAZEPINES AND 1-(AMINOMETHYL)-TRIAZOLOBENZODIAZEPINES

This invention relates to processes for converting 1-hydrogen-triazolobenzodiazepines to 1-aminomethyl-(including 1-(substituted amino)-methyl-)triazolobenzodiazepines. More particularly, this invention provides an improved process for converting estazolam-type compounds to adinazolam-type compounds through 1-hydroxymethyl- and 1-alkyl-sulfonyl-ester intermediates. Adinazolam is known to be useful for therapeutic uses.

BACKGROUND OF THE INVENTION

Gall, et al., U.S. Pat. No. 3,842,090 discloses a multi-step process for preparing 1-aminomethyl-6-phenyl-4H-s-triazolo[4,3-a][1,4]benzodiazepines, e.g., adinazolam, from 2-(unsubstituted triazolyl)benzophenones. However, for larger scale production the use of multi-step processes and time consuming column chromatography are disadvantages, which those in the art seek to avoid.

Gall, U.S. Pat. No. 4,001,262 discloses a process for preparing 1-[(dimethylamino)methyl]-6-substituted 4H-s-triazolo[4,3-a][1,4]benzodiazepines, e.g., adinazolam, by reacting a 4H-s-triazolo[4,3-a][1,4]benzodiazepine, e.g., estazolam, with a dimethyl(methylene)ammonium halide salt reagent in one step. However, that patent also reports the use of chromatography procedures in the detailed examples thereof for purifying the end product thereof.

Derwent Abstract 48681A briefs a Japanese Patent Publication No. 59696/78, published May 29, 1978, disclosing the ring closure of 2',5-dichloro-2-[3-(dimethylaminomethyl)-5-mesyloxymethyl-4H-1,2,4-triazol-4-yl]benzophenone in a sealed tube with ammonia containing methanol to obtain 8-chloro-6-(2-chlorophenyl)-1-[(dimethylamino)methyl]-4H-s-triazolo[4,3-a][1,4]benzodiazepine. However, sealed tube procedures are not practical for commercial scale chemical process operations, and the abstract does not disclose how the (3-hydroxymethyl-triazol-4-yl)-compounds are obtained.

Derwent Abstract 52339T describes a West German patent application No. 2201210 published Aug. 3, 1972 and disclosing the conversion of 1-hydroxyalkyl-triazolobenzodiazepines via a reactive ester to the corresponding 1-[(dimethylamino)methyl]triazolobenzodiazepines.

Those in the art continue to search for improved methods for making valuable drug compounds more efficiently.

OBJECTS OF THE INVENTION

It is an object of this invention to provide an improved process for preparing 1-aminomethyl-(including 1-(substituted amino)methyl-)6-substituted 4H-s-triazolo[4,3-a][1,4]benzodiazepines in high yields and without the need for column chromatography or sealed tube procedures.

It is a more specific object of this invention to provide an improved process for preparing adinazolam-type compounds from estazolam-type compounds in high yields without the need for column chromatography or sealed tube procedures.

SUMMARY OF THE INVENTION

Briefly, I have discovered that 1-hydrogen-6-substituted-4H-s-triazolo[4,3-a][1,4]benzodiazepine type compounds of Formula I, e.g., estazolam, can be converted in high yields and without using column chromatography or sealed tube procedures to 1-(hydroxymethyl)-6-substituted-4H-s-triazolo[4,3-a][1,4]benzodiazepines of Formula II, and these Formula II 1-hydroxymethyl-compounds can be converted to 1-aminomethyl-(including 1-(substituted aminomethyl-)6-substituted-4H-s-triazolo-[4,3-a][1,4]benzodiazepine compounds of Formula IV, e.g., adinazolam, by heating the above Formula I 1-hydrogen-6-substituted-4H-s-triazolo-compound with paraformaldehyde in an inert liquid solvent under essentially neutral pH conditions at a temperature sufficient to dissolve the 1-hydrogen-6-substituted-4H-s-triazolo-compounds (I) and to crack or break up the paraformaldehyde to a reactive formaldehyde form therein for a time sufficient to form the 1-hydroxymethyl-6-substitut-ed-4H-s-triazolo[4,3a][1,4]benzodiazepine (II), without extensive formation of 1,4-bis(hydroxymethyl)-group substitution;

and thereafter, if desired, converting the 1-(hydroxymethyl)-6-substituted-4H-s-triazolo-compound (II) to a 1-(sulfonyloxymethyl)-6-substituted-4H-s-triazolo-intermediate compound (III), and then reacting the 1-(sulfonyloxymethyl)-6-substituted-4H-s-triazolo-compound (III) with ammonia or the selected primary or secondary amine, e.g., with aqueous dimethylamine, to form the product 1-amino- or 1-(substituted-aminomethyl)-6-substituted-4H-s-triazolo-compound (IV), e.g., adinazolam, and recovering such product from that reaction mixture, without column chromatography.

DETAILED DESCRIPTION OF THE INVENTION

The chemical reactions and general scope of the processes of this invention can illustratively be represented by the attached chemical structures I, II, III and IV in which R is hydrogen, fluoro, chloro, bromo, trifluoromethyl or nitro;

x defines the degree of polymerization of commercially available paraformaldehyde which is used as the source of reactive formaldehyde in this process to form compound (II);

$R^1$ is the $C_1$ to $C_3$ hydrocarbon radical or other residue of the sulfonyl halide which is used to form the sulfonyl ester intermediate (III); and can be, for example, $C_1$–$C_3$-alkyl, phenyl, p-tolyl, xylyl, or the like, but is preferably methyl;

$R_2$ and $R_3$ are each hydrogen, $C_1$ to $C_3$-alkyl, or $R_2$ and $R_3$- are taken together with the nitrogen to which they are bonded to complete a mono-cyclic saturated ring having from 4 to 7 carbons and 1 to 2 nitrogens such as N-pyrrolidinyl, N-piperidinyl, N-piperazinyl or any other cyclic amine which has been suggested in the art for 1-(substituted amino)methyl group substitution on these 4H-s-triazolo[4,3-a][1,4]benzodiazepine compounds, but, it is preferred that each of $R_2$ and $R_3$ be methyl;

Z is chloro or bromo,

Y is trivalent nitrogen (—N=) to complete a 2-pyridyl ring on the structures or

where R₃ is hydrogen, chloro or fluoro, as suggested in Gall U.S. Pat. No., 4,001,262, or which is described and claimed in Hester et al. U.S. Pat. No. 4,250,094. To date, this process has been carried out in seventy-six percent (76%) yield overall (89 percent yield for the hydroxymethylation (Step 1) and 85 percent for the sulfonationamination (Steps 2 and 3).

In operation of the first step of the process we have found the process to be effective when the starting material (I), e.g., estazolam, and the paraformaldehyde are combined in the liquid diluent in ratios of about 1:0.8 to 1:1.3, respectively, although other ratios can be used.

The liquid solvent or diluent liquid which is used in the first step of the process to convert compound I to compound II can be any liquid or mixture of liquids which has a high enough boiling point to be liquid at the desired reaction temperature, which will remain inert throughout the reaction, and which will not allow for the generation of any acid or base in the mixtures as it is heated. The liquid solvent or diluent should allow for the dissolution of the compound I therein as the mixture is heated, and should be heatable as a liquid to a temperature sufficient to crack or degrade the paraformaldehyde to a reactive form of formaldehyde in the mixture. Such liquids are preferably a nonpolar, aprotic liquid which will maintain its liquid state at temperatures ranging from about 105° C. to 140° C. Examples of such liquid diluents or solvents for this purpose include toluene, xylene, halobenzenes, decalin, biphenyl, or halogenated biphenyls. As a practical matter, for reasons of economy and safety for process operating personnel, it is preferred to use xylene in this first step of the process.

If the compound I and the paraformaldehyde are heated at temperatures of from about 120° to 135° C. in xylene solution, reaction times of from 2 to 5 hours, usually less than 4 hours reaction time, are sufficient to convert essentially all of the compound I to the compound II in these mixtures. If a lower reaction temperature is used, say, when toluene is used, (b.p. 110.6° C.) as the solvent, longer reaction times will be needed. But it is believed to be important to terminate further reaction between the compound I and paraformaldehyde after no more than about 5 hours.

When the compound I to compound II reaction is completed to the desired extent, the reaction mixture can be treated by conventional chemical procedures, without use of column chromatography procedures to separate a crude compound II intermediate product which is pure enough to use in the next step of the process to convert compound II to compound III and then to compound IV without needing to use column chromatography purification procedures. For example, the reaction mixture containing the 1-(hydroxymethyl)-compound II can be decanted hot to separate the liquid reaction mixture from any unreacted paraformaldehyde and then the solvent can be removed by vacuum concentration procedures to leave the crude 1-hydroxymethyl-compound II as a residue. Alternatively, the Step 1 reaction can be filtered hot, and the solvent removed by vacuum concentration of the filtrate. The residue from either procedure can be: (1) used as is in the next process step without further prior processing; (2) dried, if desired, by dissolving the residue in a solvent such as methylene chloride, drying with a suitable anhydrous salt such as sodium sulfate, filtering the mixture and evaporating the solvent to provide a dried residue which is used in the next process step; or (3) recrystallized, after drying as in (2) above if desired, from an appropriate solvent or solvent mixture such as ethyl acetate-Skellysolve B ® brand of hexanesmethanol to provide a purified 1-(hydroxymethyl)-compound for use in the next process step or for use as the active drug component of the appropriate pharmaceutical formulation. The 1-(hydroxymethyl)-compound from each procedure can then be dissolved or diluted in an appropriate liquid such as a halogenated alkane, e.g., methylene chloride, ethylene dichloride, chloroform, carbon tetrachloride, benzene, xylene, toluene, tetrahydrofuran and the like, for the next step.

The 1-(hydroxymethyl)-compound II in appropriate solution in a low or high boiling solvent such as tetrahydrofuran (THF), a halogenated alkane such as methylene chloride, chloroform, carbon tetrachloride or in a hydrocarbon solvent such as hexane, cyclohexane, heptane, benzene, toluene, xylene, is then contacted at low to mild temperature, with sufficient, usually a slight molar excess of a hydrocarbyl-sulfonyl halide, as indicated above, preferably methanesulfonyl chloride or bromide, or other C₁ to C₃-alkanesulfonyl chloride or bromide, p-toluenesulfonyl chloride or bromide, or other economical sulfonyl source, in the presence of a hydrogen halide scavenging base, such as a trialkylamine, e.g., trimethylamine, triethylamine, bis(isopropyl)ethylamine, or dimethylaniline, and the like, and cooled as necessary to control any exothermic heat of reaction which may occur, to form the respective sulfonyl ester compound III. This esterification reaction is run at −20° C. to 30° C., preferably 0° C. to 10° C., such that the solvent medium remains liquid. This esterification reaction, with the choice combination of reactants is usually quite swift, but the mixture can be stirred and be allowed to warm as necessary to ensure substantially complete reaction.

This esterification reaction mixture can be washed with dilute aqueous base solutions to remove any remaining hydrogen halide by-product, concentrated to remove the bulk of the organic diluent or solvent, and then the crude sulfonyl ester compound III can be diluted in tetrahydrofuran or other diluent such as methylene chloride, benzene, toluene, or xylene, and treated with the selected amine or ammonia (which can be used in excess to scavenge the acid liberated) in aqueous, organic or mixed aqueous-organic mixture to convert the sulfonyl ester III to the amine product. This amination reaction also usually occurs quickly at room temperature, but the mixture can be stirred for a time sufficient to ensure complete conversion of the ester III to the amine IV.

We have stirred this reaction mixture up to 20 hours, but from later repetitions of the process we learned such extensive stirring times are not essential for efficient operation of the process.

The amine product (IV) of the process can be recovered from its above reaction mixture, without column chromatography by conventional chemical procedures. The reaction mixture can be extracted with a suitable solvent for the amine product IV such as ethyl acetate, methylene chloride or chloroform to separate it from salt by-products and solvent materials. The organic solvent solution of the amine product can be washed with water, aqueous base, and aqueous salt solution to remove impurities which are soluble in those aqueous media. The product extract can be dried to remove water and concentrated to leave as residue the crude amine product IV. The amine product IV can be further purified and crystallized by dissolution in appropriate solvent, e.g., ethyl acetate, Skellysolve B ® brand of hexanes, or mixtures thereof, and the mixture can be allowed to stand or cooled to effect crystallization of the amine product IV. The crystalline product IV can be separated from the crystallization solvent, dried, and thereafter used as the active drug component of the appropriate pharmaceutical formulation.

Examples of compounds which can be prepared by the herein described method are those exemplified and set forth in the above referenced U.S. Patents, Gall Nos. 3,842,090, Gall 4,001,262, as well as the products of Hester, Jr., U.S. Pat. No. 4,250,094, the lead compound example of which is 8-chloro-1-[(dimethylamino)methyl]-6-phenyl-4H-s-triazolo[4,3-a][1,4]benzodiazepine, now known generically as adinazolam, as well as 8-Bromo-1-[(dimethylamino)methyl]-6-(2-pyridyl)-4H-s-triazolo[4,3-a][1,4]benzodiazepine, and other related compounds described in Hester, Jr., U.S. Pat. No. 3,995,043.

The process is further described and illustrated by the following detailed examples.

EXAMPLE 1

A. 1-(HYDROXYMETHYL)-8-CHLORO-6-PHENYL-4H-s-TRIAZOLO[4,3-a][1,4]BENZODIAZEPINE (0.017 Mole Scale)

Into 120 ml of hot xylene (about 120° C.) there was dissolved 5.0 g of 8-chloro-6-phenyl-4H-s-triazolo-[4,3-a][1,4]benzodiazepine (estazolam) within about 10 minutes with stirring. To this solution there was then added 5.0 g of paraformaldehyde solid. The mixture was continuously heated at 125° to 130° C. After about 30 minutes of heating a sample of the reaction mixture was taken for thin layer chromatography (TLC) analysis. Samples of the reaction mixture and the starting material (estazolam) were spotted and compared with a mixture of both the starting material and the reaction mixture on the TLC plate using 15 percent methanol in chloroform v/v as the developing liquid and an iodine chamber for visualization so that the spots could be seen.

The TLC test indicated that the reaction was not yet complete so another 1 g of paraformaldehyde was added 45 minutes after the first. Heating of the reaction mixture was continued at 125° C. After 1.5 hours total heating, a second TLC sample was taken and analyzed as above and it indicated that the estazolam was almost all consumed. To ensure complete reaction, another 0.5 g of paraformaldehyde was added and heating of the mixture was continued at 125° C. for another 45 minutes (2.25 hours total heating time), at which time testing by TLC analysis indicated reaction was substantially complete to form 1-(hydroxymethyl)-8-chloro-6-phenyl-4H-s-triazolo[4,3-a][1,4]benzodiazepine.

The hot reaction mixture was a water clear liquid. It was decanted from the reaction vessel flask into a 500 ml single necked, round bottomed flask and concentrated in vacuo at 80° C. to a white glass consistency. The crude product weighed 5.8 g. A Nuclear Magnetic Resonance spectrum (NMR) analysis of this product was consistent with the desired product with a trace of xylene and water present. There was no evidence of any 1,4-bis(hydroxymethyl) substitution.

This crude glassy product was dissolved in 25 ml of methylene chloride, dried with anhydrous sodium sulfate and transferred to a 250 ml single neck, round bottomed flask and again concentrated in vacuo at 90° C. to a glassy white solid weighing 5.43 g (about 100% yield). No chromatography procedure was necessary to purify this 1-hydroxymethyl intermediate for further reaction.

B. CONVERSION OF 1-(HYDROXYMETHYL)-8-CHLORO-6-PHENYL-4H-s-TRIAZOLO-[4,3-a][1,4]BENZODIAZEPINE TO 1-[(N,N-DIMETHYLAMINO)METHYL]-8-CHLORO-6-PHENYL-4H-s-TRIAZOLO-[4,3-a][1,4]BENZODIAZEPINE (ADINAZOLAM) (0.014 Mole Scale)

In a single necked, round bottomed flask there was added 4.51 g (0.014 mole) of the crude 1-(hydroxymethyl)-8-chloro-6-phenyl-4H-s-triazolo[4,3-a][1,4]benzodiazepine, from Step (A) above, and 2.0 g of N,N-(diisopropyl)ethylamine in 25 ml of methylene chloride cooled to about 0° C. using an ice/water bath. To the cooled mixture there was added dropwise a solution of 1.80 g (0.0157 mole) of methanesulfonyl chloride (mesyl chloride) in about 20 ml of methylene chloride. A TLC aliquot sample of the reaction mixture immediately after the addition of the mesyl chloride had been completed indicated no starting material remained. The ice bath was removed and the orange colored solution was allowed to warm near room temperature. The reaction mixture was washed once with water and then with dilute sodium bicarbonate aqueous solution. The methylene chloride layer was concentrated in vacuo at 40° C. to a pink colored glassy 1-(methanesulfonyloxymethyl) ester intermediate. An NMR of a sample confirmed the presence of the methane sulfonyl ester. The weight of this crude ester was 6.40 g.

The crude glassy methanesulfonate ester was dissolved in 25 ml of tetrahydrofuran (THF) and then 25 ml of aqueous dimethylamine was added. The golden color of the mixture turned immediately to blood red during an exothermic reaction which occurred. Within 10 minutes the temperature of the mixture returned to room temperature. The color of the mixture was then golden. A TLC analysis of the mixture indicated the reaction was not quite complete so the reaction mixture was allowed to stir at room temperature under nitrogen atmosphere for 20 hours to ensure substantially complete reaction. A TLC analysis of the reaction mixture evidenced that there was only one major product; no 1,4-addition of hydroxymethyl→sulfonate ester→diamine reaction had occurred.

The THF was removed from the reaction mixture in vacuo. The aqueous residue was extracted twice with ethyl acetate. The ethyl acetate extracts were combined and washed as one phase with about 50 ml of water, once with 50 ml of aqueous 10 percent sodium hydroxide solution, once again with water, once with saturated sodium chloride solution, and then dried over anhydrous sodium sulfate and concentrated in vacuo to leave as residue 5.46 g of glassy solid product. This product was redissolved in about 75 ml of ethyl acetate and treated with about 1 g of Darco-brand of decolorizing charcoal. The mixture was allowed to stand for 10 minutes and filtered to separate the charcoal. The charcoal did not help much in removing color. The ethyl acetate was removed in vacuo to leave a glassy solid weighing 5.12 g.

Ethyl acetate was added. Crystals began to form, so the mixture was heated on a steam bath to redissolve the suspended crystals. The mixture was gravity filtered into an Erlenmeyer flask. The mixture was concentrated on a steam bath to about a 30 ml volume, and then about 70 ml of hexane was added. Then the mixture was allowed to stand overnight at ambient temperature (about 20°–22° C.) to allow crystallization to occur.

The mixture was then filtered, and the solid was washed with a 1:1 v/v ethyl acetate/hexane mixture. The first crop of off-white crystalline adinazolam weighed 3.35 g, m.p. 165°–166° C. The melt was light yellow and clear. An NMR spectral analysis of this material was good evidence for adinazolam.

The mother liquor was concentrated on a steam bath. Ethyl acetate and Skellysolve B were added, and the mixture was allowed to stand to permit further crystallization. The resulting crystals (2nd crop) were separated by filtration, and weighed 0.40 g and were white in color. The yield of the first and second crops combined was 3.75 g (76% yield), m.p., 164°–166° C. The NMR spectrum of this material was consistent for adinazolam.

The second crop mother liquor still appeared to contain product, adinazolam, along with some unreacted 1-(hydroxymethyl)-8-chloro-6-phenyl-4H-s-triazolo[4,3-a][1,4]benzodiazepine starting material.

EXAMPLE 2

A. 1-(HYDROXYMETHYL)-8-CHLORO-6-PHENYL-4H-s-TRIAZOLO[4,3-a][1,4]BENZODIAZEPINE (0.1 Mole Scale)

In a 2-liter, three-necked, round bottomed flask, equipped with a condenser, thermometer, sand bath for heating and mechanical stirrer there was added 29.6 g (0.1 mole) of estazolam, and then 700 ml of stock xylene which had been stored over molecular sieves to dry it. The resulting mixture was heated to 130±5° C. internal temperature until solution of estazolam in the xylene was accomplished. Then 15 g of paraformaldehyde was added; some foaming occurred. The internal temperature was slowly reduced from about 135° C. to 118° C. as paraformaldehyde dissappeared. The mixture was stirred about 15 minutes and a sample of the reaction mixture was taken for TLC analysis. The TLC indicated that the reaction mixture still contained about 40 percent of the original estazolam starting material.

After 45 minutes from initial addition of paraformaldehyde, another 10 g of paraformaldehyde was added at about 110° C. The resulting mixture was stirred for another 30 minutes and another TLC analysis indicated no estazolam starting material was present. The resulting reaction mixture was gravity filtered while hot into a round bottomed flask. The reaction flask was rinsed with 50 ml of warm xylene, and the rinse was also passed through the filter into the round bottomed flask containing the filtrate. The xylene was removed from the flask in vacuo at 90° C. to essential dryness of the residue, which weighed 30.8 g for a 95% yield. There was a slight odor of xylene and possibly of formaldehyde. An NMR spectral analysis (CDCl3 solvent; also with deuterium oxide added to exchange the OH proton) was run on the glassy foam.

The sides of the reaction flask were rinsed with methylene chloride and the resulting solution was concentrated, and a sample was taken for NMR analysis.

A portion of this crystalline product (5.25 g) was recrystallized from a mixture of ethyl acetate and Skellysolve B ® brand of hexanes containing some methanol. Filtration provided a first crop of the above titled compound, 4.45 g, m.p. 191.5–192.5. The NMR spectral analysis (as above) was very reasonable for the titled 1-(hydroxymethyl) compound. A second crop of crystalline product was obtained from the filtrate, 0.46 g, m.p. 190.5°–192° C. (water-clear melt), for a total weight of 4.92 g (94% yield). A third NMR analysis of this material was very reasonable for the titled 1-(hydroxymethyl) material.

B. CONVERSION OF 1-(HYDROXYMETHYL)-8-chloro-6-phenyl-4H-s-TRIAZOLO[4,3-a][1,4]BENZODIAZEPINE TO 1-[(N,N-DIMETHYLAMINO)METHYL]-4H-s-TRIAZOLO[4,3-a][1,4]BENZODIAZEPINE (ADINAZOLAM) (6.2 Mmole Scale)

To a suspension of 2.00 g (6.2 mmoles) of 1-(hydroxymethyl)-8-chloro-6-phenyl-4H-s-triazolo[4,3-a][1,4]benzodiazepine, prepared as described above, in 25 ml of THF at 0° C. (ice bath cooling) under a nitrogen atmosphere there was added 0.8 g of triethylamine. Then, to the resulting stirred mixture there was added 0.8 g of mesyl chloride in 10 ml of THF dropwise over 10 minutes. The resulting slight pinkish white mixture was stirred for 10 minutes, after which a sample was taken for TLC analysis. The TLC analysis showed essentially complete conversion of the 1-(hydroxymethyl)-starting material to the methanesulfonate ester intermediate.

Then at 0° C. with ice bath cooling, 10 ml of 40% aqueous dimethylamine solution was added dropwise within 0.5 minute. A sample for TLC analysis was taken within 1 minute. The mixture was stirred for 5 more minutes. The mixture was then concentrated in vacuo to an aqueous residue which was then extracted with 50 ml of ethyl acetate. The extract was washed once with water, once with dilute aqueous sodium bicarbonate solution, once more with water, and then with saturated aqueous sodium chloride solution, and then dried with anhydrous sodium sulfate and concentrated in vacuo to leave as residue 2.20 g of a glassy solid. A sample for NMR spectral analysis was taken, and the remainder was dissolved in a mixture of ethyl acetate:Skellysolve B ®. The solid which formed was filtered and washed with Skellysolve B to produce 1.83 g (84.7% yield), m.p. 168°–70° C. of adinazolam. After vacuum drying the adinazolam crystals 20 minutes at 60° C., the NMR spectrum was very reasonable for adinazolam product.

Hence, these examples show that the yields of this process are approximately as follows, with no column chromatography being required.

From estazolam to the 1-(hydroxymethyl)-8-chloro-6-phenyl-4H-s-triazolo[4,3-a][1,4]benzodiazepine (95% crude; 89% crystallized yield in two crops);

From the 1-(hydroxymethyl)-compound, through the mesyl chloride esterification to adinazolam (85% yield, first crop), for an overall yield from estazolam starting material to adinazolam product of approximately 75.7% yield, m.p. 168°–170° C., with no column chromatography.

Analysis of the adinazolam product of this process was as follows:

Anal. Calc. for $C_{19}H_{18}ClN_5$ (mol wt 351.18) % Calcd: C, 64.98; H, 5.17; N, 19.94; Cl, 10.10 % Found: C, 64.98; H, 5.15; N, 19.94; Cl, 10.06 Re-test: C, 64.81; H, 5.16; N, 19.71

The Infrared (IR), Mass Spectral (MS), Ultraviolet (UV) spectral analyses all supported the named adinazolam product.

Thus the process of this invention for converting a compound of the formula I to a compound of the formula IV via intermediate compounds of the formulas II and III provides a surprisingly and unexpectedly high yield of final product IV without requiring a column chromatography. Furthermore the nature of this process, and particularly the absence of any column chromatography, makes the process eminently suitable for practical and economical production scale operation.

TABLE 1

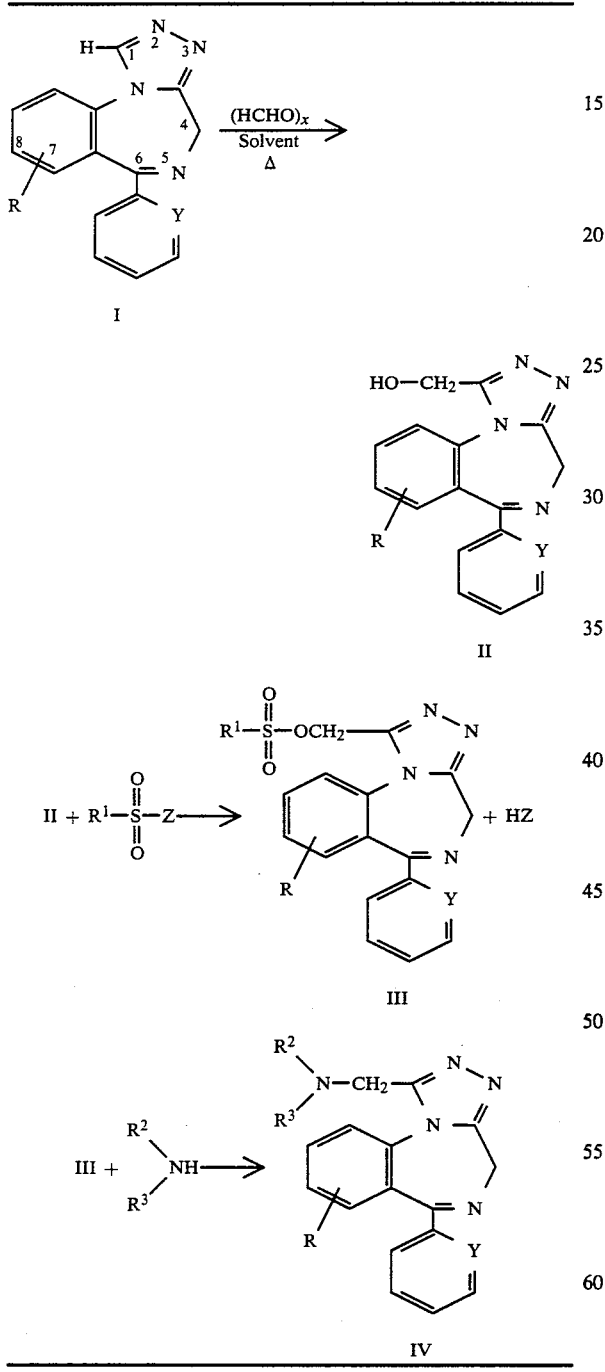

I claim:
1. A process for preparing a 1-aminomethyl-6-substituted-4H-s-triazolo[4,3-a][1,4]benzodiazepine of the formula

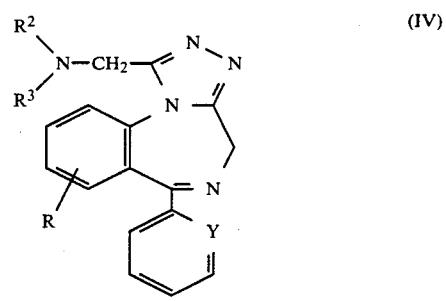

wherein R is hydrogen, fluoro, chloro, bromo, trifluoromethyl or nitro $R_2$ and $R_3$ are each hydrogen, $C_1$ to $C_3$-alkyl, or $R_2$ and $R_3$ are taken together with the nitrogen to which they are bonded to complete a monocyclic, saturated amine ring; selected from the group consisting of N-pyrrolidinyl, N-piperidinyl and N-piperazinyl and Y is a trivalent nitrogen or a $-CR_3=$moiety where $R_3$ is hydrogen, fluoro or chloro;

which comprises heating a mixtutre of paraformaldehyde and a compound of the formula

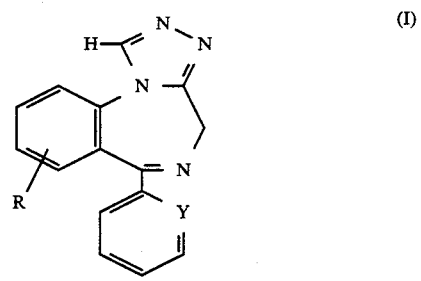

where R and Y are as defined hereinabove, in an inert liquid solvent under essentially neutral pH conditions at atmospheric pressure and at a temperature sufficient to dissolve the compound (I) therein and to crack the paraformaldehyde to a reactive form of formaldehyde for a time up to about 5 hours to form a 1-(hydroxymethyl)-compound of the formula

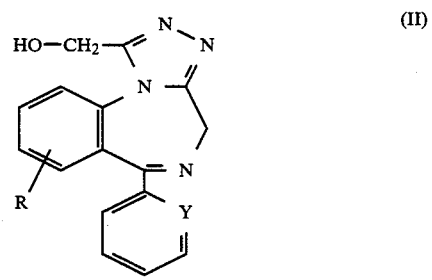

wherein R and Y are as defined hereinabove, without formation of 1,4-bis(hydroxymethyl)-substitution separating the 1-hydroxymethyl-product (II) from its preparation mixture without using column chromatography procedures;

contacting and reacting the 1-(hydroxymethyl) compound of Formula II with a sulfonyl compound of the formula

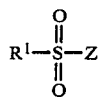

where $R^1$ is $C_1$ to $C_3$-hydrocarbon radical, and Z is chloro or bromo, for a time sufficient to form a sulfonate ester of the formula

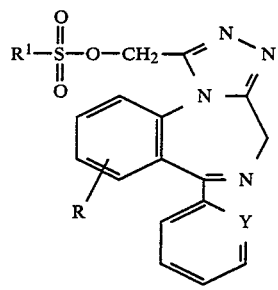

where R, $R^1$ and Y are as defined above, and contacting and reacting the sulfonyl ester compound III with a compound of the formula

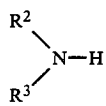

Where $R^2$ and $R^3$ are as defined above, in an aqueous, organic, or mixed aqueous-organic medium to form the 1-aminomethyl compound of Formula IV, and recovering the 1-aminomethyl compound of Formula IV without the need for column chromatography procedures.

2. A process according to claim 1 wherein estazolam, a Formula I compound is converted to 1-(hydroxymethyl)-8-chloro-6-phenyl-4H-s-triazolo[4,3-a][1,4]benzodiazepine, a Formula II compound;

the Formula II compound is converted to 1-(methanesulfonyloxymethyl)-8-chloro-6-phenyl-4H-s-triazolo[4,3-a][1,4]benzodiazepine, a formula III compound, and the Formula III compound is converted to adinazolam, a Formula IV compound.

3. A process according to claim 2 wherein estazolam is reacted with paraformaldehyde in xylene at 120° C. to 140° C. for a time sufficient to form 1-(hydroxymethyl)-8-chloro-6-phenyl-4H-s-triazolo[4,3-a][1,4]benzodiazepine;

the hereinabove 1-(hydroxymethyl)-compound is reacted with methanesulfonyl chloride to form the 1-(methanesulfonyloxymethyl)-compound; and the hereinabove 1-(methanesulfonyloxymethyl) compound is reacted with dimethylamine to form adinazolam.

4. A process for preparing a 1-(hydroxymethyl)-6-substituted-4H-s-triazolo[4,3-a][1,4]benzodiazepine of the formula

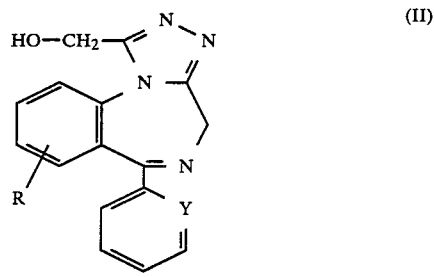

wherein R is hydrogen, fluoro, chloro, bromo, trifluoromethyl or nitro, and Y is a trivalent nitrogen or a —$CR_3$=moiety where $R_3$ is hydrogen, fluoro or chloro, which comprises heating a mixture of paraformaldehyde and a compound of the formula

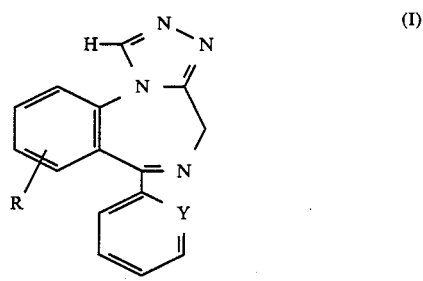

wherein R and Y are as defined hereinabove, in an inert solvent under essentially neutral pH conditions at atmospheric pressure and at a temperature sufficient to dissolve the compound (I) therein and to crack the paraformaldehyde to a reactive form of formaldehyde for a time sufficient to form a 1-(hydroxymethyl)-compound of the Formula II, without extensive formation of 1,4 bis(hydroxymethyl)-substitution, and separating the 1-hydroxymethyl-product II from its preparation mixture without using column chromatography procedures.

5. A process according to claim 4 wherein estazolam, a Formula I compound, is converted to 1-(hydroxymethyl)-8-chloro-6-phenyl-4H-s-triazolo[4,3-a][1,4]benzodiazepine, a Formula II compound.

* * * * *